US00PP26612P3

(12) United States Plant Patent
Johansson

(10) Patent No.: US PP26,612 P3
(45) Date of Patent: Apr. 19, 2016

(54) **MAPLE TREE (*ACER TRUNCATUM*) NAMED 'BABY DRAGON'**

(50) Latin Name: *Acer truncatum*
Varietal Denomination: Baby Dragon

(71) Applicant: Keith G. Johansson, Arlington, TX (US)

(72) Inventor: Keith G. Johansson, Arlington, TX (US)

( * ) Notice: Subject to any disclaimer, the term of this patent is extended or adjusted under 35 U.S.C. 154(b) by 76 days.

(21) Appl. No.: 13/815,604

(22) Filed: May 22, 2013

(65) Prior Publication Data

US 2014/0352013 P1 Nov. 27, 2014

(51) Int. Cl.
*A01H 5/00* (2006.01)
*A01H 5/04* (2006.01)

(52) U.S. Cl.
USPC ..... Plt./224
CPC ..... *A01H 5/04* (2013.01)

(58) Field of Classification Search
USPC ..... Plt./224
See application file for complete search history.

(56) References Cited

U.S. PATENT DOCUMENTS

| | | | |
|---|---|---|---|
| PP4,654 | P | 2/1981 | Siebenthaler |
| PP11,295 | P | 3/2000 | Moon |
| PP11,322 | P | 4/2000 | Hanson |
| PP17,367 | P3 | 1/2007 | Johansson |

*Primary Examiner* — Susan McCormick Ewoldt
(74) *Attorney, Agent, or Firm* — Guy V. Manning

(57) ABSTRACT

A novel variety of the maple tree *Acer truncatum* was discovered in North Texas. It has a distinct dwarf size and prolific, very small leaves which weigh down its thin, willowy branches, giving it a weeping bushy habit. It exhibits distinctive, pink new growth which persists throughout spring and summer and into fall, whereupon it develops striking, deep yellow and red fall colors. The variety known as 'Baby Dragon' also is highly tolerant to direct summer sun and low-light conditions alike, as well as drought conditions, especially for a dwarf variety.

9 Drawing Sheets

Latin name of the genus and species and the variety denomination of the plant claimed: *Acer truncatum* 'Baby Dragon'.

BACKGROUND OF THE INVENTION

1. Field of the Invention

This invention relates generally to decorative maple trees known by the scientific name *Acer truncatum* and the common name "Shantung" maple, and particularly to a new and distinct variety thereof identified as *Acer truncatum* 'Baby Dragon'. I discovered it growing in a cultivated area in my nursery in Fort Worth, Tex., in 1994. I have given it the name 'Baby Dragon' because of its dwarf size and miniature leaves.

No federally sponsored research or development was involved in this invention.

2. Background

Maple trees provide desirable shade from spring to fall and typically shed their leaves for winter, thereby providing useful surrounding vegetation where summer sunlight may be excessive and winter sunshine is desirable. Displaying striking colors, maple trees are characteristically ornamental and provide pleasing and varying visual effects throughout their foliage period.

The *Acer truncatum* maple tree, commonly called "Shantung" maple, is a newly introduced tree in the United States which does exceptionally well in the Midwest in hot climates and heavily alkaline soils. Typical fifteen year old Shantung maple trees stand upright and are twenty-eight to thirty-four feet tall, with a spread of twenty to twenty-six feet. Shantung maple leaves generally are characterized by having truncated base lobes near the leaf petiole and by having a prominent central lobe, giving the leaf a distinctly ovate-truncate shape. Fall foliage appears yellow, with occasional areas of lesser reds or orange mixed with yellow, though the latter seldom is repeated in subsequent years.

The instant novel variety of maple tree now discovered is a dwarf variety with small leaves that is ideally suited for rock gardens and foundation planting. 'Baby Dragon' maples have thin, willowy branches that give it a weeping, bushy appearance. It always seems to be growing vigorously, but never gets big. The original tree is seventeen years old and only 4'-10" tall. The tree is a distinctive dwarf maple that should grow to only two (2) meters or so in height and have a dense, weeping, rounded crown with a greater spread than height.

The instant novel variety of maple tree also exhibits vibrant spring and summer new growth colors and not the reddish-purple or green new growth as typical of many Shantung maples. A 'Baby Dragon' maple's new growth is pink and exhibits a rare, strong pink in summer. It also exhibits deep yellow and red fall colors similarly to Shantung, but produces more consistent mixed fall colors than typical.

The instant novel variety of maple tree also is a very adaptable and hardy tree that withstands full sun in the Midwest and lower South, whereas other dwarf (typically Japanese) maples easily burn in direct summer sunlight.

SUMMARY OF THE INVENTION

The novel cultivar of the present invention, named *Acer truncatum* 'Baby Dragon,' is believed to be a variant of an unknown *Acer truncatum* distinguished by its dwarf size, willowy weeping bushy habit, good heat and sun tolerance, and a consistent pink new growth color throughout the spring and summer, developing striking deep yellow and red coloration variations in the fall. Specifically:

(a) its dwarf stature results in a small tree ideally suited for gardens and foundation growth;

(b) its very small but prolific leaves weigh down its thin, willowy branches, leading to a weeping appearance;

(c) its distinctive pink new growth persists throughout spring and summer and into fall, whereupon it develops deep yellow and red fall colors; and (d) is highly tolerant to direct summer sun and low-light conditions alike, as well as drought conditions, especially for a dwarf variety.

DETAILED DESCRIPTION OF THE INVENTION

The instant variety of maple tree was discovered as a seedling growing among a group of other maple tree seedlings of the *Acer truncatum* species at my nursery in Fort Worth, Tex., in 1994. It was successfully asexually reproduced at said nursery by grafting onto other *Acer truncatum* seedlings and by semi-hardwood cuttings. The novel characteristics are reliably transmitted to succeeding generations.

With reference to the seventeen (17 y.o.) year old trees depicted in the figures, the following specific description of the instant maple variety details its unique characteristics. Color terminology refers to The 2001 Royal Horticultural Society (R.H.S.) Colour Chart.

Origin: A tree of unknown origin, a 'Baby Dragon' maple is similar to other *Acer truncatum* varieties except for its dwarf size, small leaves, small flowers, thin willowy branches and overall weeping and spreading appearance. Its new growth also exhibits a distinctive, strong pink color (RHS 48C) throughout spring and summer. 'Baby Dragon' maples are notably tolerant of both shaded and direct sun and heat conditions, and hardy to at least Zone 5 and possibly Zone 4. 'Baby Dragon' maples also are prodigious leaf producers, which weighs down their thin, willowy branches. Its leaves are unusually small for Shantung maples, though proportionate to the dwarf size of the tree itself.

Classification: *Acer truncatum* 'Baby Dragon'.

Parentage: Unknown; believed to be a seedling variation, mutation or adaptation of *Acer truncatum.*

Figure 1A:
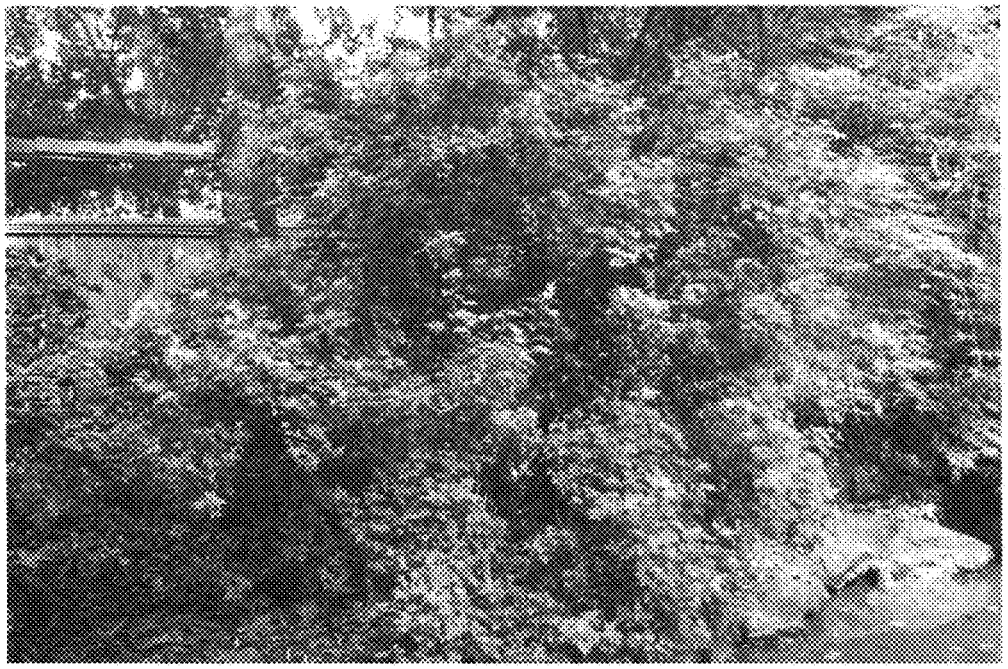
FIG. 1A is a photographic view of one example of a mature original tree of the present invention, showing the willowy, spreading, weeping bushy habit during summer foliage.
Figure 1B:
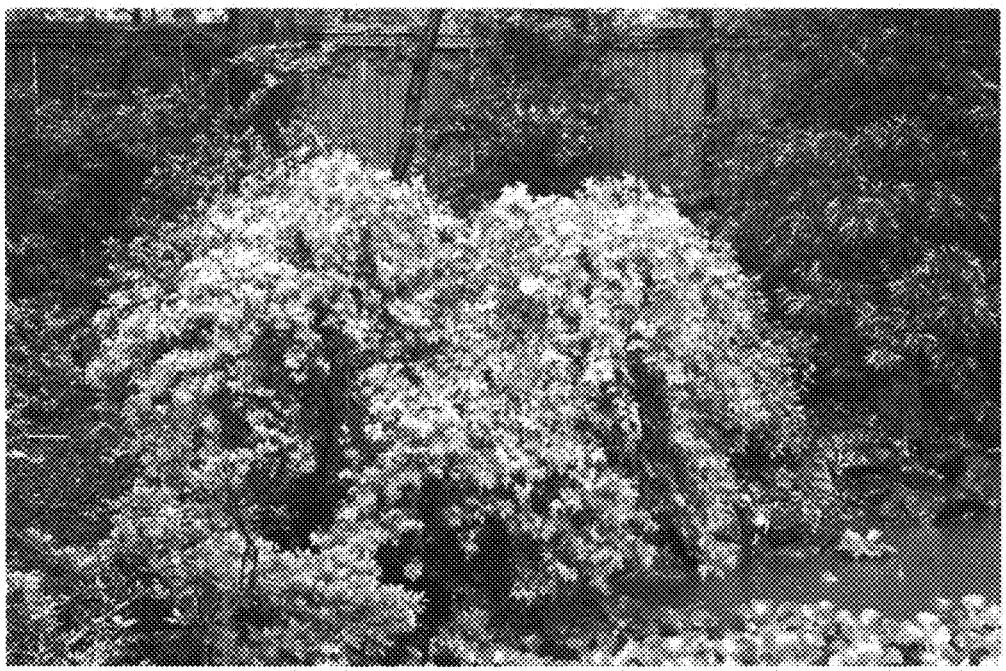
FIG. 1B is a photographic view of another example of a mature original tree of the present invention, showing another view of the willowy, spreading, weeping, bushy habit during summer foliage similar to the example of the present invention shown in FIG. 1A.

Shape: Deciduous tree with rounded crown of uniform spread, wider than it is tall, with many vigorous, crowded stems which are thin and willowy, resulting in a weeping appearance under the load of its profuse leafy foliage in spring and summer. See FIGS. 1A-1B. Caliper size is three (3 cm) centimeters inches in four (4) years, on grafts measured eighteen (18") inches up from ground level.

Height: Four feet (4'-10") ten inches (147.3 cm) tall for the mature, 17 year old tree of FIG. 1A. A three year graft was measured at four feet (4'-2") two inches (127 cm) tall, indicating a very slow change in height despite vigorous annual new growth and leaf production, much smaller that typical of *Acer truncatum*. See FIGS. 1A-1B.

Spread: Six feet (6'-1") one inch wide for the mature, 17 year old tree of FIG. 1A. A three year graft was measured at four feet (4'-9") nine inches (144.8 cm) wide. This indicates a bushy, low growing dwarf variety that changes size very little despite vigorous new growth and leaf production, much less than typical of *Acer truncatum*. See FIGS. 1A-1B.

Figure 2A:
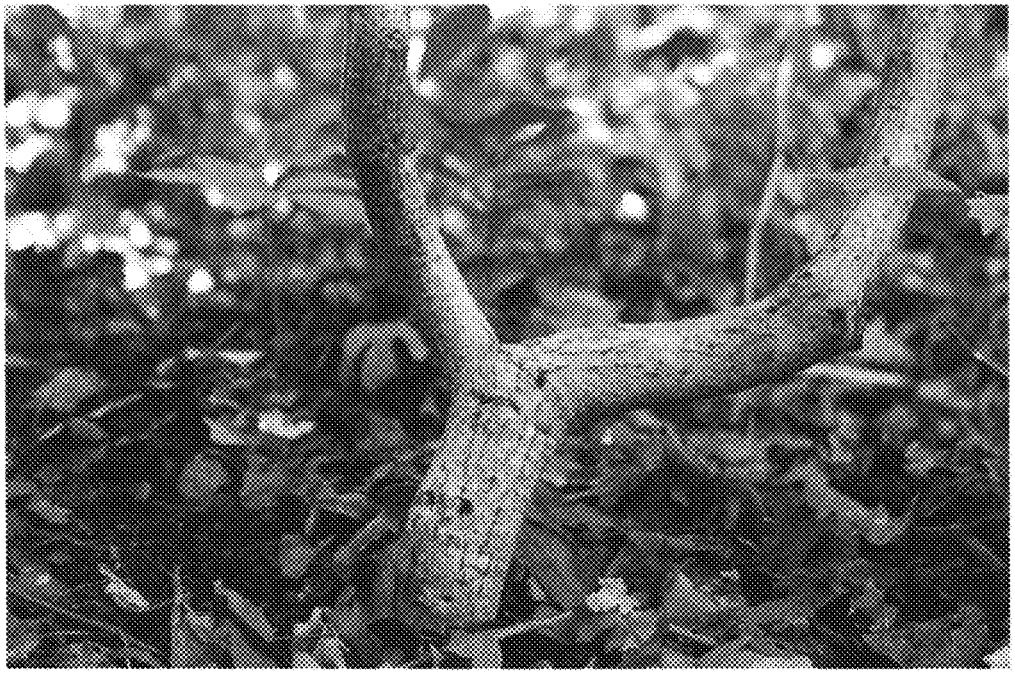
FIG. 2A is a photographic close-up view of the trunk and low major branches of the mature original tree of FIG. 1A.
Figure 2B:
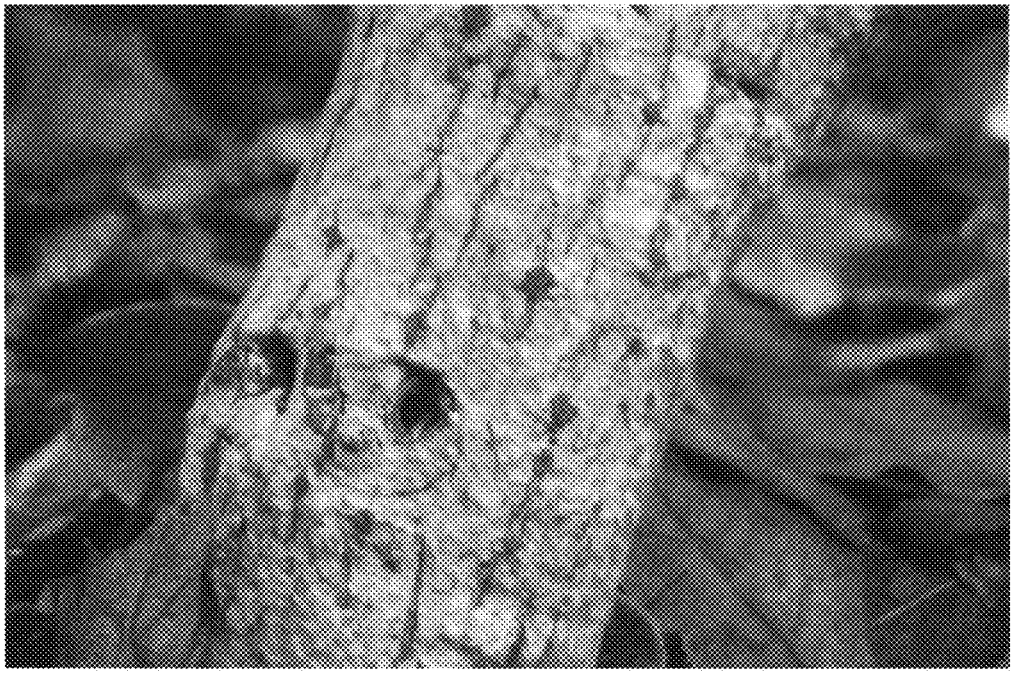
FIG. 2B is a photographic close-up of the trunk of the mature original tree of FIG. 1A and showing bark characteristics.
Figure 2C:
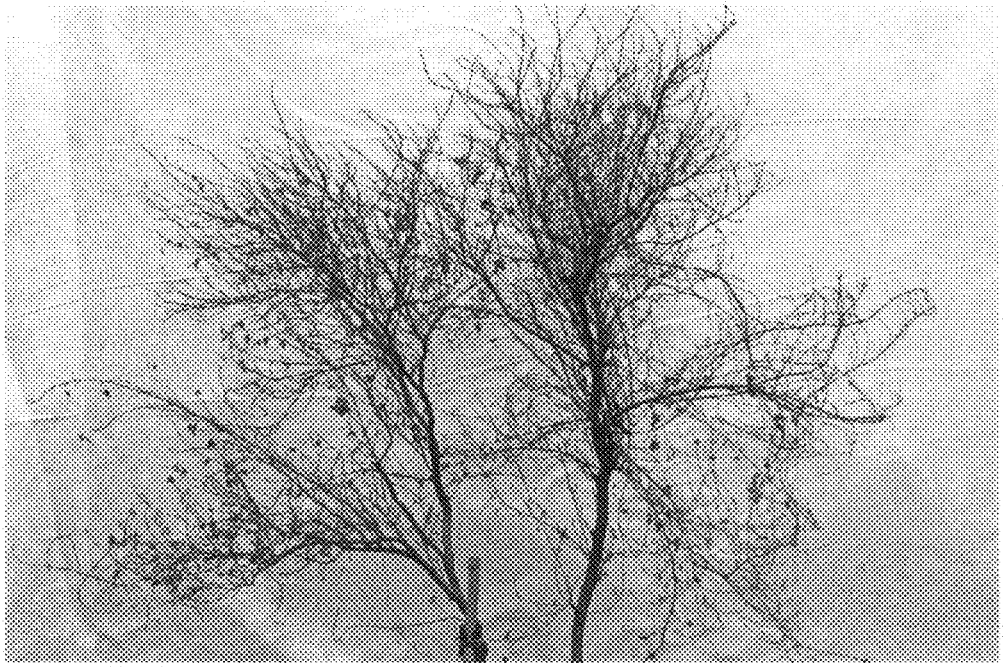
FIG. 2C is a photographic view of the mature original tree of FIG. 1A and exhibiting its willowy, thin branch structure.

Trunk: Original trees have smooth, light yellowish gray (RHS 156) bark due to their low caliper growth rate. See FIGS. 2A-2B. Grafted trees exhibit heavily fissured bark, with light yellowish gray (RHS 156) raised areas and yellowish brown (RHS 199C) recessed areas, typical of the normal Shantung root stock but in smaller scale. Caliper size of an original tree (the 17 year old tree of FIG. 1A) is four (4 cm) centimeters, while a three (3) year old graft on *Acer truncatum* root stock already has a three (3 cm) centimeter caliper.

Branches: Noticeably thin and willowy, as well as closely and thickly branching. Current year wood starts as the same color as the leaves, but quickly becomes light gray (RHS 156C). Late season current shoots can display a darker, red-brown (RHS 165B) and yellow-brown (RHS 165C) color in winter, similar to the leaf but darker. First and second year wood is pliable, becoming hard and dense in its third year. Lenticils are sparse, straw-colored and oval.

Leaves:

*Size*.—Much smaller than *Acer truncatum;* 20.2 (20.2 mm) millimeters long by 23.1 (23.1 mm) millimeters wide. Largest sampled: 33 mm by 40 mm. Smallest sampled: 8 mm by 10 mm.

*Shape*.—Cordate base with only occasionally truncate base typical of *Acer truncatum*. Glabrous with five (5) oblong-ovate lobes, deeply cut two-thirds of way from tip to leaf base. Margins entire and slightly wavy. Small, triangular teeth on central lobes, sometimes also found on one or more neighboring lobes. Central lobes are broader at the bottom and triangular-ovate. Acuminate apices and tufted, veined axils on the underside.

Figure 4A:
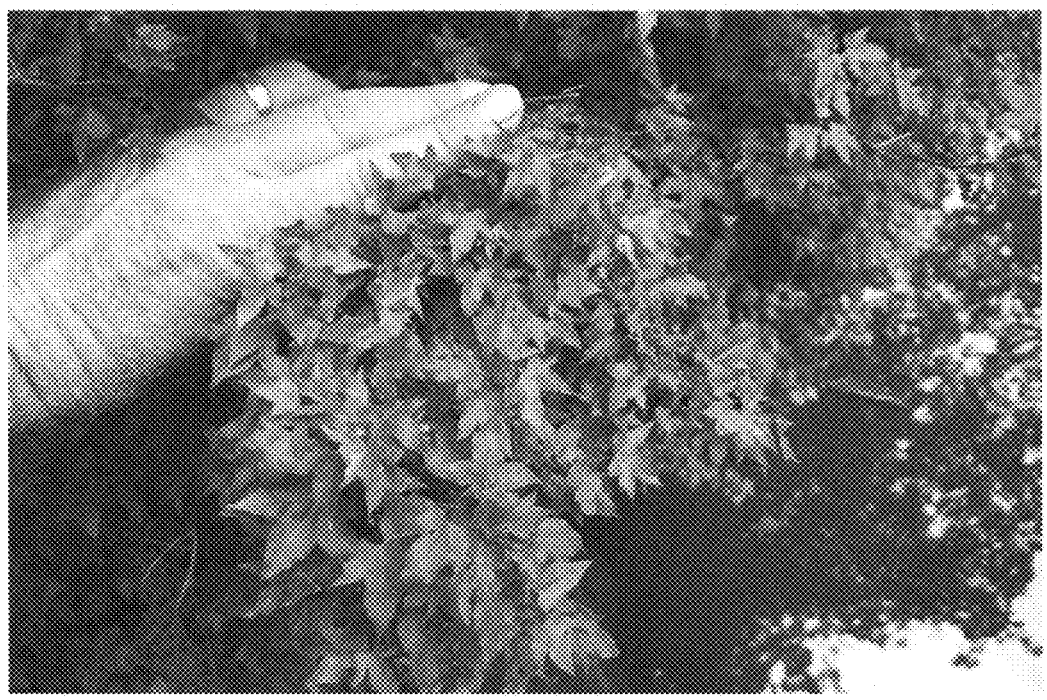
FIG. 4A is a photographic close-up of a branch of growth leaves on the mature original tree of FIG. 1A, illustrating the size (juxtaposed to a man's hand) and vigorous profusion of leaves on a typical branch of the mature original tree of FIG. 1A.
Figure 4B:
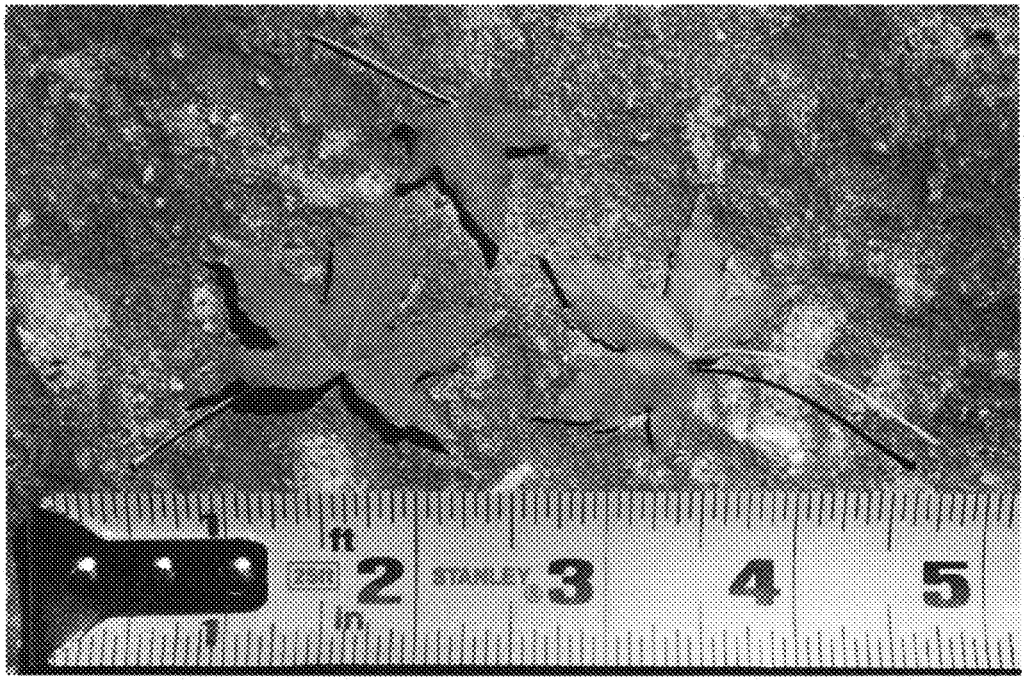
FIG. 4B is a photographic view of individual leaves of the mature original tree of Figure 1A and showing actual size against a measuring tape.
Figure 5A:
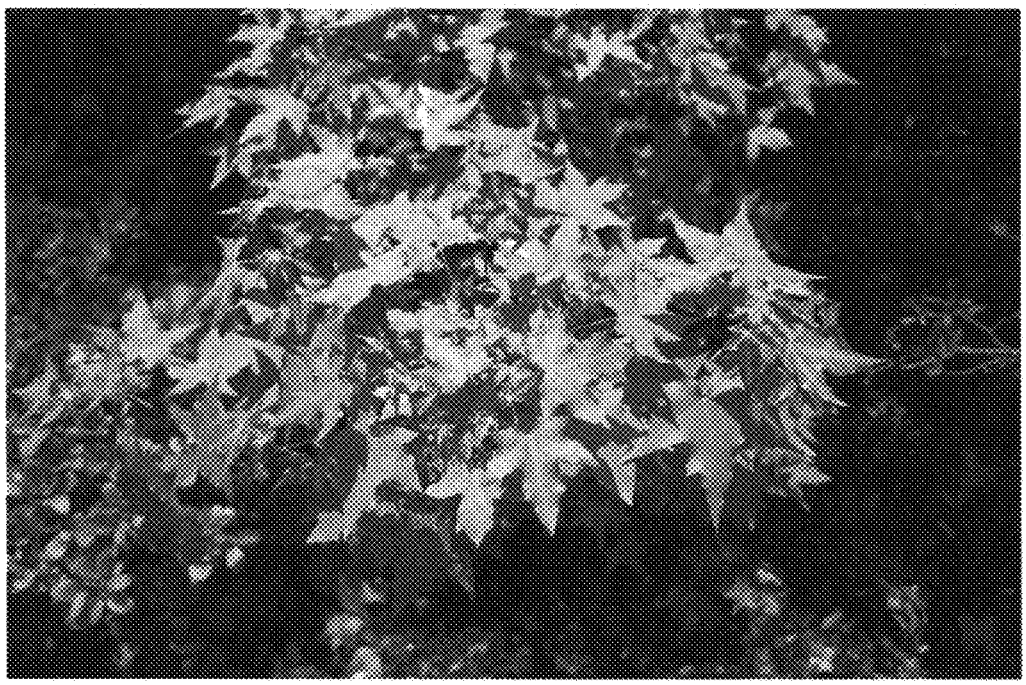
FIGS. 5A-5C are photographic distance and close-up views of the early flush deep pink coloration of new growth on the mature original tree of FIG. 1A.
Figure 5B:
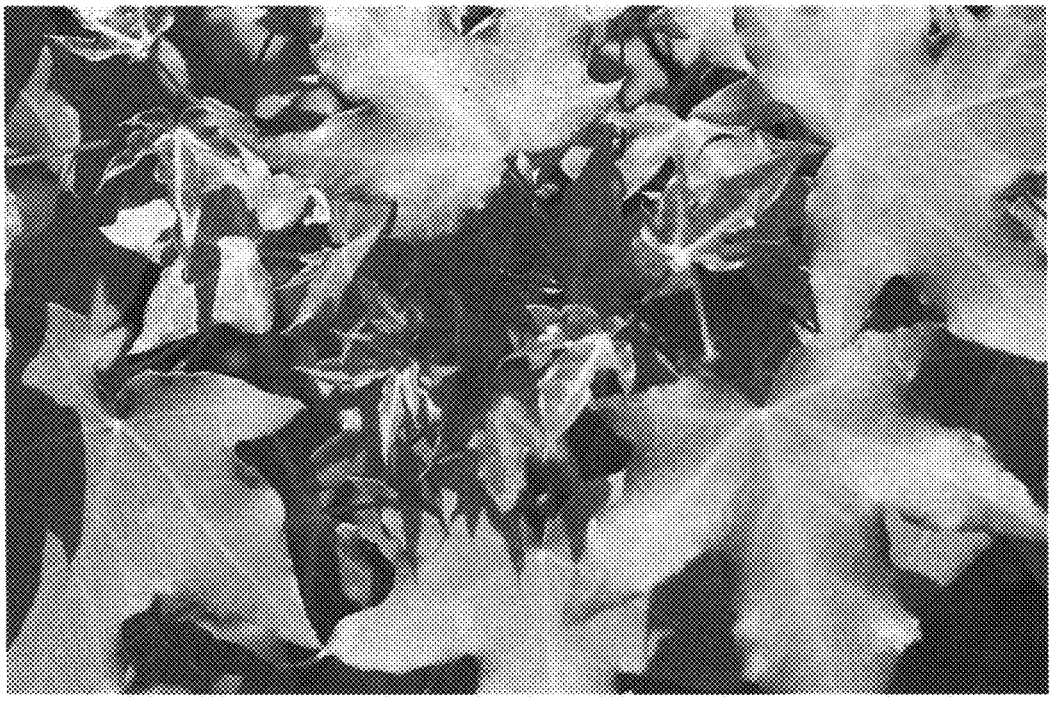
Figure 5C:
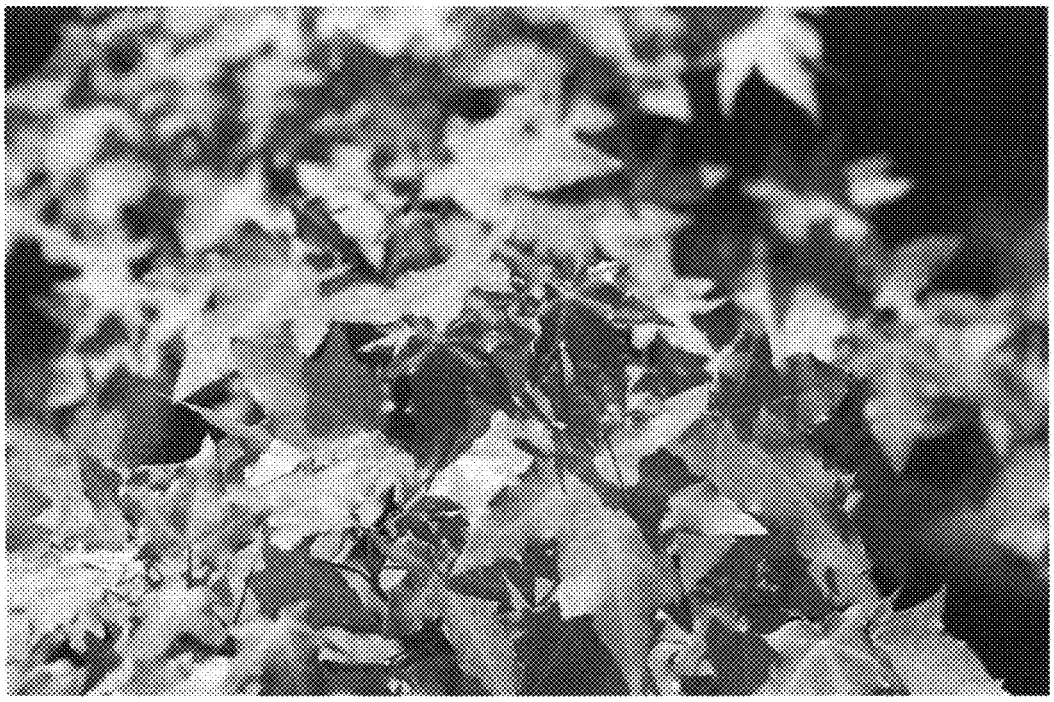
Figure 6A:
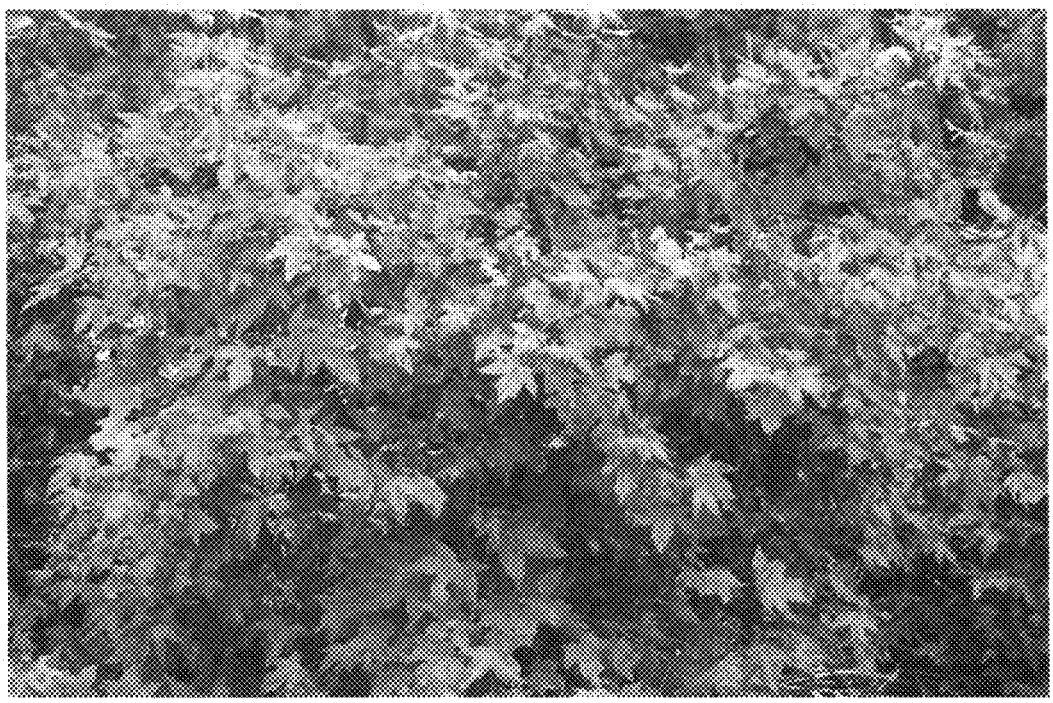
FIGS. 6A and 6B are photographic distance and close-up views of the particularly striking strong pink of summer growth on the mature original tree of FIG. 1A.
Figure 6B:
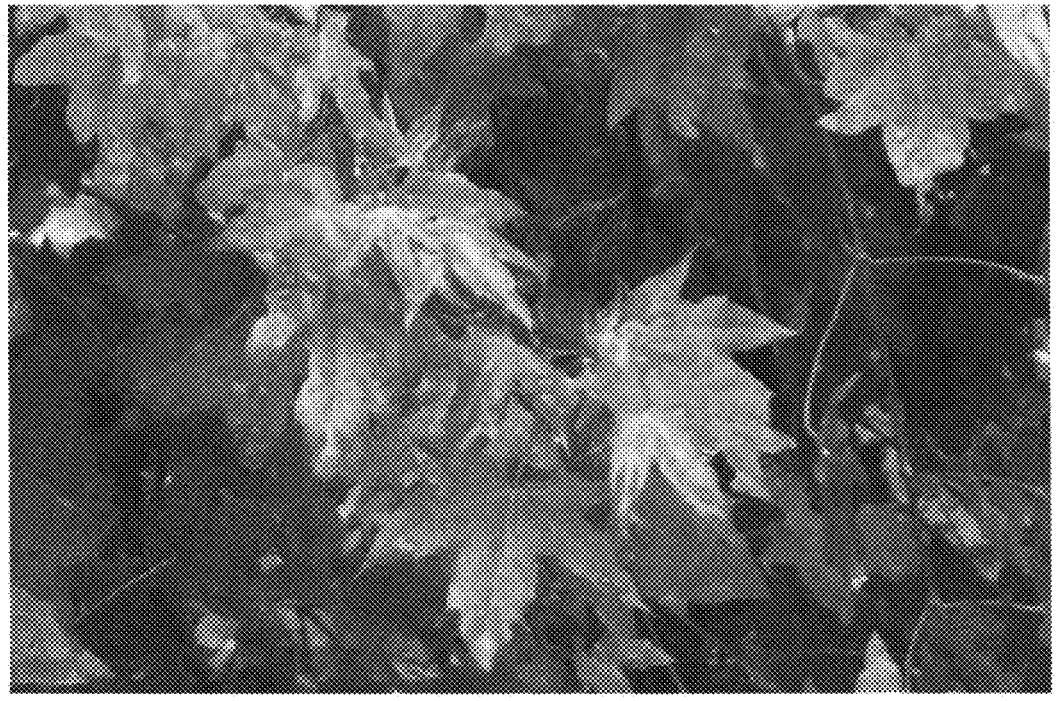
Figure 7A:
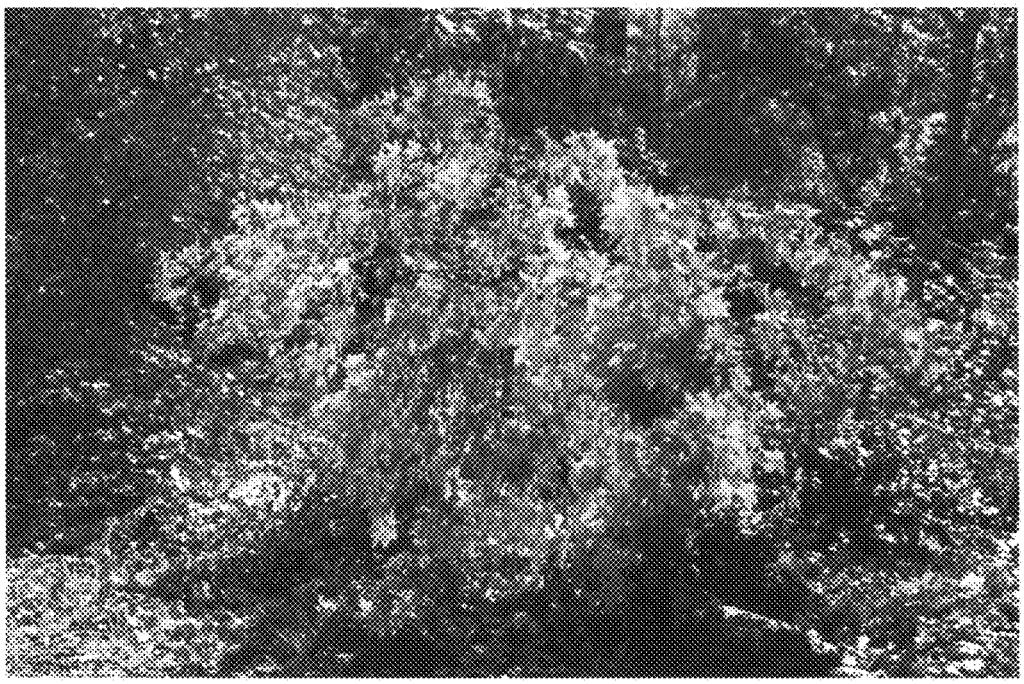
FIGS. 7A and 7B are photographic distance and close-up views of the deep yellow and red fall colors of the mature original tree of FIG. 1A.
Figure 7B:
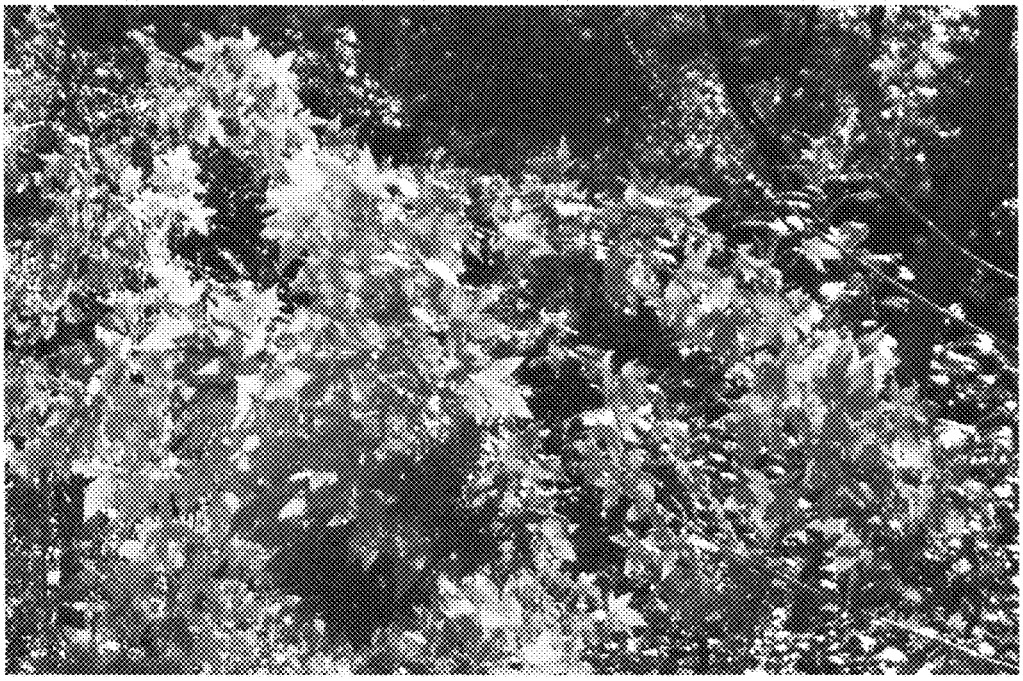
Figure 8A:
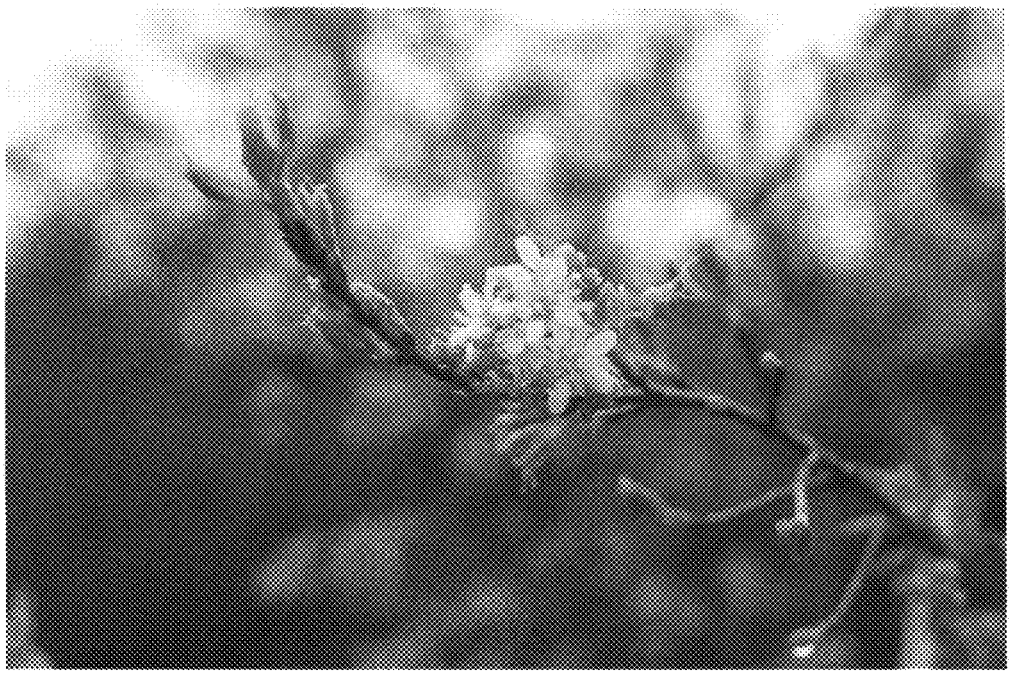
FIGS. 8A and 8B are photographic close-up views of flowers produced recently by the mature original tree of FIG. 1A.
Figure 8B:
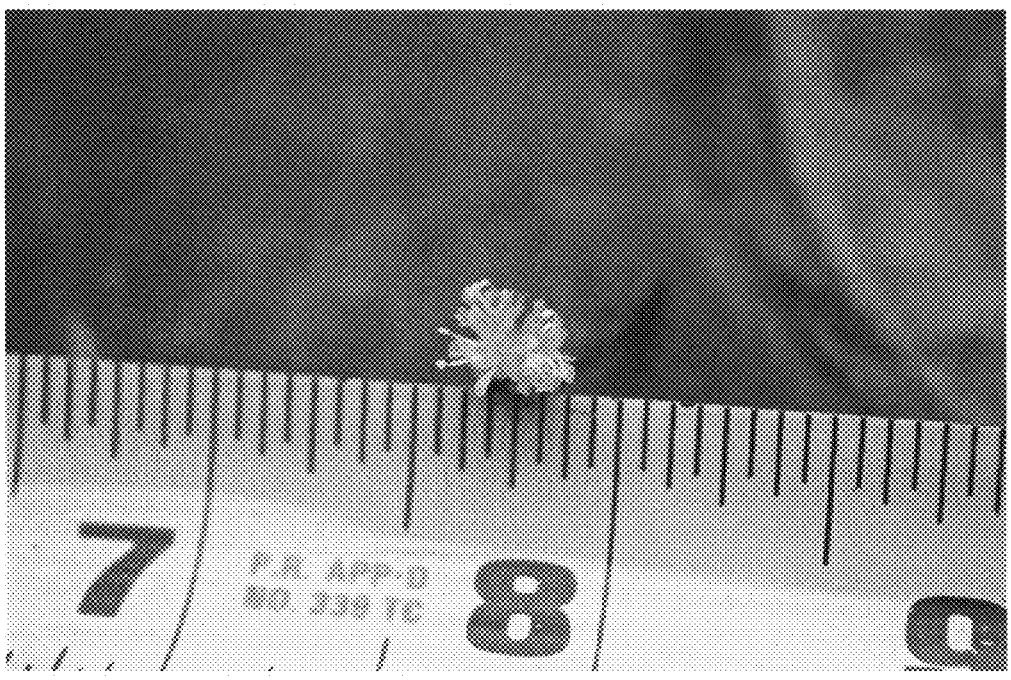

*Color*.—Waxy cuticle typical of *Acer truncatum* creating a glossy shine at certain angles of sunlight, but not as dark green or shiny as *Acer truncatum*. Leaves are the same color on top and bottom, with prominent, raised veins on the bottom appearing disproportionate due to the small leaf size. See FIGS. 4A, 5B. Vibrant spring and summer new growth foliage. Deep yellow and red fall colors. Colors on new growth are intense, deep pink and rare, strong pink in summer, in contrast to typical purplish-red Shantung colors. Early flush is deep pink (RHS 48A), turning in early spring to deeper pink (RHS 48B). See FIGS. 5A-5C. Summer growth is distinctive, strong pink (RHS 48C). See FIGS. 6A-6B. Fall colors become deep yellow (RHS 4C) to red (RHS 34C). See FIGS. 7A-7B. Hardened. mature growth foliage has a shiny green (RHS 140) on the leaf top with the same coloration on both the tops and bottoms of the leaves. Not as dark green or glossy as typical Shantung. See FIGS. 4A-4B.

Petiole: Slender, same red color as new growth, keeping a lighter red color on the sunny top side all summer. Small, averaging 17.7 mm in length, glabrous. Milky sap produced when broken.

Figure 3A:
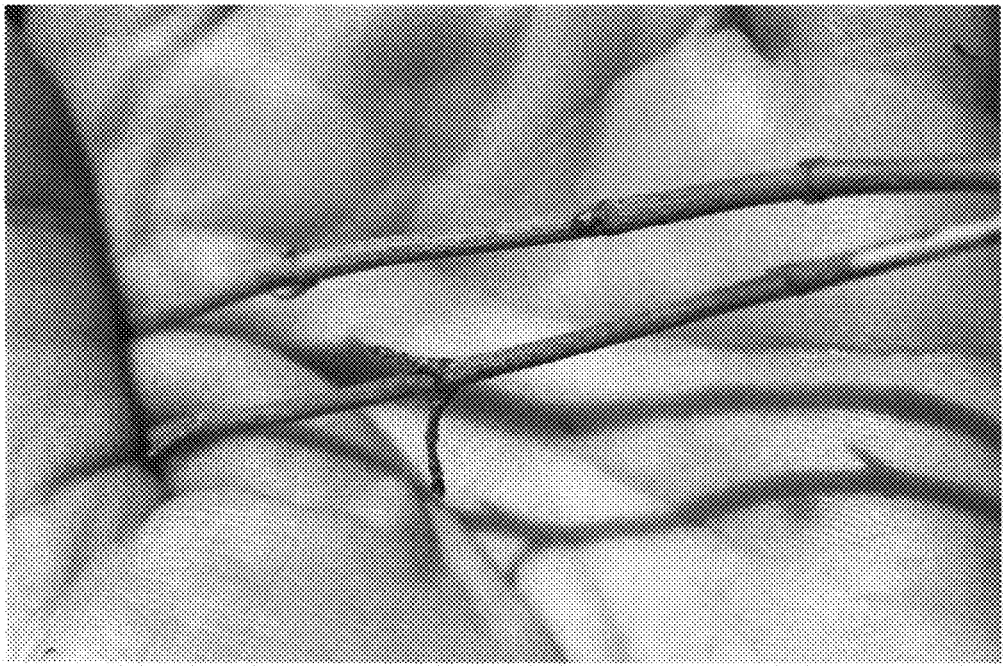
FIGS. 3A and 3B are photographic close-up views of lateral and terminal buds, respectively, of the mature original tree of FIG. 1A.
Figure 3B:
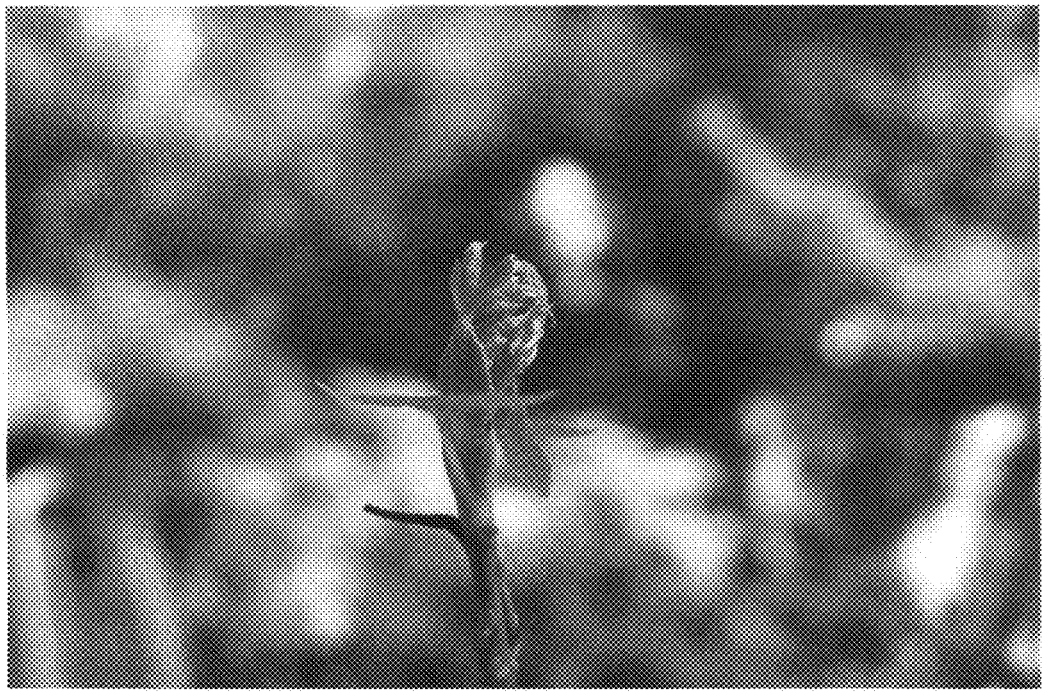

Winter buds: Terminal buds maximum of three (3 mm) millimeters long by two (2 mm) millimeters wide, but can be much smaller; usually brown-gray. Current year shoots sometimes long but much thinner (3 mm) than normal Shantungs. Lateral buds very small (1 mm×0.5 mm). See FIG. 3A.

Flowering: Flowering season is spring (mid-March in Texas), before or simultaneously with leaves on terminal, twenty by twenty to thirty (20×20-30 mm) millimeter corymbose racemes having unequal, five to ten (5-10 mm) millimeter length stems. Each 5-merous bloom is deep saucer-shaped, three (3 mm) millimeters long and four (4 mm) millimeters deep, with oblong to ovate petals and supported on five (5 mm) millimeter pedicels. Light Greenish Yellow (RHS 8C) color.

Reproductive organs: Imperfect; monoecious; trees first produce blooms of one gender, then of the other, then of the first again, often having both at the same time; approximately half of the trees begin with each gender. Blooms have a central circular, slightly lobed light greenish yellow (RHS 8C) pistil with an ovary supported by two divergent stigma arms with short half (0.5 mm) millimeter styles. Pistil is surrounded by eight one-half (0.5) millimeter, glabrous stamens with numerous oval, one-half (0.5) millimeter anthers on two (2 mm) millimeter filaments. In male flowers, filaments are longer, sometimes extending the anthers above the perianth, with a diminished pistil and vestigial ovary. Female blooms have shorter filaments wherein the smaller anthers are almost concealed within the perianth.

Pollen: Same color as flowers (Light Greenish Yellow-RHS 8C).

Fruit: None observed to date.

Disease resistance: No known problems.

Climate: Adapts well to any well-drained soil, even highly alkaline, clay soils. Very drought, wind and direct sunlight tolerant. Extremely hardy to at least Zone 5 and possibly to Zone 4 (USDA hardness guidelines). 'Baby Dragon' maples start growing one to two weeks earlier than *Acer truncatum* and have been observed on several occasions in full leaf in ambient temperatures of 24 degrees Fahrenheit without damage. More drought and sunshine tolerant than other *Acer* dwarf varieties, especially dwarf Japanese maple varieties, and it exhibits a good ability to keep healthy new growth without wilting under extreme heat and direct, intense sunlight conditions, as well as thriving in shady environments.

In comparison to *Acer truncatum* species, 'Baby Dragon' maples demonstrate:

*Crown*.—Similar rounded crown, but wider than height atypical of *Acer truncatum*, which is taller that it is wide at a similar age; overall height and spread of 'Baby Dragon' expected to be much smaller.

*Trunk*.—Smooth, less fissured, light yellowish gray bark on original trees; grafted examples have heavily fissured trunk, with light yellowish gray raised areas between dark, yellowish brown fissures, typical of *Acer truncatum* but smaller in scale.

*Flowers*.—Similar straw-yellow, but half the size of those for *Acer truncatum*.

*Reproductive organs*.—Similar to *Acer truncatum* but half the size; monoecious imperfect, pollen same color as blooms.

*Fruit*.—None observed to date but expected to be smaller.

*Leaf shape and size*.—Much smaller than *Acer truncatum* species leaves; average 2.0 cm long by 2.3 cm wide, compared with seven to thirteen (7-13 cm.) centimeters across for normal Shantung leaves. Only occasionally truncated, five oblong-ovate lobes; deep cut two-thirds of way from tip to leaf base; and a larger, central lobe that is broader at the bottom and triangular-ovate, producing an overall cordate-palmate leaf shape.

*Mature leaves*.—Green (RHS 140C), though not as dark green or glossy as typical *Acer truncatum* species. Leaves are not lighter green on the bottom (typical of *Acer truncatum* leaves) but the same color on top and bottom, with prominent, raised veins on the bottom appearing disproportionate due to the small leaf size.

*Spring color*.—Pink (RHS 48A), segueing into brighter pink (RHS 48B), in contrast to normal reddish-purple (RHS 60D) of *Acer truncatum* species.

*Summer color*.—Rare strong pink (RHS 48C) which persists throughout summer. Underlying mature, green leaves contrast with the pink, giving the tree a striking, pink haloed appearance throughout summer.

*Fall color*.—Fall coloration is consistently a deep yellow (RHS 4C) mixed with red (RHS 34C), whereas other *Acer truncatum* leaves are mostly yellow, with only occasional areas of lesser red or orange mixed with yellow, and seldom repeated in subsequent years.

*Hardiness*.—As drought and sunshine tolerant as larger *Acer truncatum* species, and more so than other dwarf maple cultivars. Exhibits good ability to keep healthy new growth without wilting under extreme heat and direct, intense sunlight conditions. Seems to thrive equally well in sunshine or shade. Adapts well to any well-drained soil, even highly alkaline, clay soils. Very drought, wind and direct sunlight tolerant. Extremely hardy to at least Zone 5 and possibly to Zone 4 (USDA hardness guidelines). 'Baby Dragon' has never been damaged by late spring or early fall freezes despite its early spring or late fall production of leaves.

I claim:

1. A new and distinct variety of an *Acer truncatum* maple tree named 'Baby Dragon', as described and illustrated herein.

* * * * *